US012086990B1

(12) United States Patent
Kadrmas

(10) Patent No.: US 12,086,990 B1
(45) Date of Patent: Sep. 10, 2024

(54) SYSTEMS AND METHODS FOR SIMULTANEOUS IMAGING OF MULTIPLE POSITRON EMISSION TOMOGRAPHY (PET) TRACERS

(71) Applicant: MultiFunctional Imaging LLC, South Ogden, UT (US)

(72) Inventor: Dan J. Kadrmas, South Ogden, UT (US)

(73) Assignee: MultiFunctional Imaging LLC, South Ogden, UT (US)

( * ) Notice: Subject to any disclaimer, the term of this patent is extended or adjusted under 35 U.S.C. 154(b) by 0 days.

(21) Appl. No.: 18/643,544

(22) Filed: Apr. 23, 2024

(51) Int. Cl.
  *G06T 7/11* (2017.01)
  *G16H 30/40* (2018.01)
(52) U.S. Cl.
  CPC .............. G06T 7/11 (2017.01); G16H 30/40 (2018.01); *G06T 2207/10104* (2013.01)
(58) Field of Classification Search
  CPC ............ G06T 7/11; G06T 2207/10104; G16H 30/40
  See application file for complete search history.

(56) References Cited

U.S. PATENT DOCUMENTS

| 7,848,557 B2 | 12/2010 | Kadrmas et al. |
| 10,175,216 B2 | 1/2019 | Kadrmas et al. |
| 10,765,382 B2 | 9/2020 | Liu et al. |
| 11,730,430 B2 | 8/2023 | Alpert et al. |
| 11,894,141 B2 * | 2/2024 | Baker ................... G16H 15/00 |
| 11,937,962 B2 * | 3/2024 | Sj?strand .............. G16H 15/00 |
| 11,941,817 B2 * | 3/2024 | Richter ................. G16H 50/50 |
| 2008/0230703 A1 * | 9/2008 | Kadrmas .............. G01T 1/2985 250/363.03 |
| 2018/0133350 A1 * | 5/2018 | Zanzonico ......... A61K 51/1057 |
| 2018/0303438 A1 * | 10/2018 | Hu ....................... A61B 6/5217 |
| 2019/0104940 A1 * | 4/2019 | Zhou .................... G06T 11/008 |

(Continued)

OTHER PUBLICATIONS

Bartel, T. "F18-fluorodeoxyglucose positron emission tomography in the context of other imaging techniques and prognostic factors in multiple myeloma" Blood, Sep. 3, 2009 vol. 114, No. 10, pp. 1-9. (Year: 2009).*

(Continued)

*Primary Examiner* — Mia M Thomas
(74) *Attorney, Agent, or Firm* — Amster, Rothstein & Ebenstein LLP

(57) ABSTRACT

A system and method for simultaneous imaging of multiple positron emission tomography (PET) tracers in which digital data including PET information associated with at least two time points is received, where the digital data is generated by PET scans of a region of interest of a physiologic body which has been administered at least two PET tracers that differ from one another at least in their radioactive decay constant. At least one set of output digital data is determined based on the radioactive decay constants of each PET tracer, the at least one set of output digital data corresponding to at least one of the at least two PET tracers. The determination of at least one set of output digital data includes at least one of regularizing to account for statistical noise, preconditioning the digital data to be more amenable to signal separation, applying feature preservation techniques, or accounting for late tracer kinetics.

18 Claims, 6 Drawing Sheets

(56) References Cited

U.S. PATENT DOCUMENTS

| | | | | |
|---|---|---|---|---|
| 2019/0317171 | A1* | 10/2019 | Nayak | G01R 33/5601 |
| 2019/0365341 | A1* | 12/2019 | Chan | G06T 7/0012 |
| 2020/0289077 | A1* | 9/2020 | Bai | A61B 6/584 |
| 2020/0311914 | A1* | 10/2020 | Zaharchuk | A61B 6/037 |
| 2021/0052233 | A1* | 2/2021 | Kaplan | G16H 50/30 |
| 2021/0106848 | A1* | 4/2021 | Vija | A61N 5/1075 |
| 2022/0001043 | A1* | 1/2022 | Wilson | G01N 33/566 |
| 2022/0211258 | A1* | 7/2022 | Westwick | A61B 1/0005 |
| 2022/0375612 | A1* | 11/2022 | Baker | G16H 50/20 |
| 2023/0360794 | A1* | 11/2023 | Lyu | G16H 50/20 |
| 2023/0363725 | A1* | 11/2023 | Li | A61B 6/5205 |
| 2023/0401769 | A1* | 12/2023 | Bharkhada | A61B 6/5205 |

OTHER PUBLICATIONS

Huang et al., "An Investigation of a Double-Tracer Technique for Positron Computerized Tomography," J. Nucl. Med., vol. 23, No. 9, 1982, pp. 816-822.

Kadrmas et al., "Methodology for Quantitative Rapid Multi-Tracer PET Tumor Characterizations," Theranostics 2013, vol. 3, Issue 10, Oct. 4, 2013, pp. 757-773.

* cited by examiner

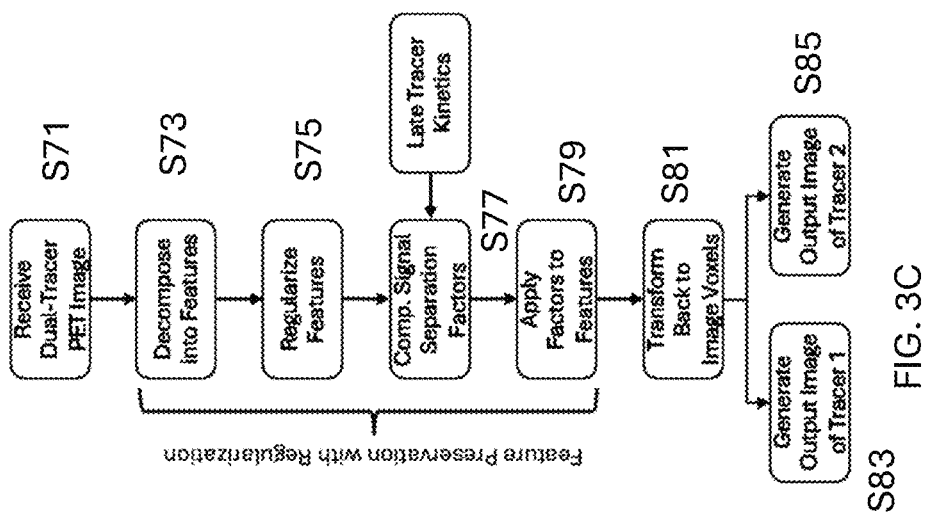
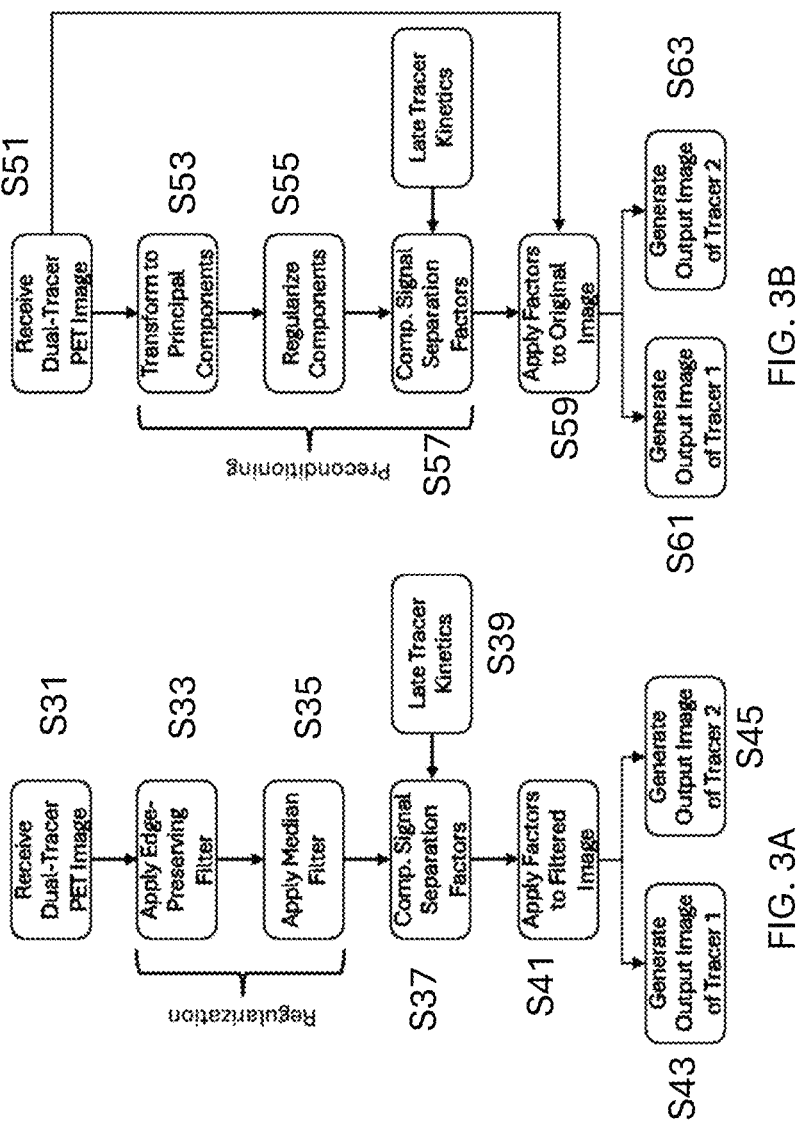
FIG. 3A
FIG. 3B
FIG. 3C

SYSTEMS AND METHODS FOR SIMULTANEOUS IMAGING OF MULTIPLE POSITRON EMISSION TOMOGRAPHY (PET) TRACERS

TECHNICAL FIELD

The present disclosure relates to diagnostic imaging, and in particular to positron emission tomography (PET) and other diagnostic modes in which a subject is examined and an image of the subject is reconstructed from the information obtained during the examination.

BACKGROUND

Positron emission tomography (PET, including PET/CT and PET/MRI) is a medical imaging modality that has important roles in oncology, cardiology, neurology, inflammation, and others. PET involves administering and imaging a radiopharmaceutical "tracer", where different tracers provide very different information. For example, F18-fluorodeoxyglucose (FDG) is a tracer that images glucose metabolism, and PET imaging of FDG plays a key role in diagnosing and staging a wide variety of malignant tumors, assessing tumor grade, and evaluating response to therapy. Similarly, N13-ammonia is a tracer that images blood flow to tissues, and cardiac PET imaging of N13-ammonia is used to diagnose coronary artery disease and guide treatment decisions. Numerous other PET tracers have been studied for imaging a wide variety of targets and applications, and the number of PET tracers that have been approved for routine clinical use is rapidly increasing each year.

One unique aspect of PET is that different tracers can provide very different and complementary information. As such, imaging with two or more PET tracers can provide much more information than imaging with a single tracer. Without loss of generality consider, for example, cancer imaging with recently-approved theranostic tracers. Such theranostic tracers measure different aspects of tumor function as compared to traditional diagnostic tracers like FDG, they provide complementary images with different detection and staging performance across different levels of tumor differentiation and grade, and they can directly predict the performance of certain targeted therapies.

Representative examples of recently-approved theranostic PET tracers include Ga68 DOTATATE for somatostatin receptor (SSTR) imaging of neuroendocrine tumors (NETs), and Ga68 PSMA-11 for imaging prostate-specific membrane antigen (PSMA)-positive lesions. Each of these theranostic tracers has a therapeutic analog (e.g. Lu177-DOTATATE and Lu177-PSMA, respectively), and uptake of these tracers can predict effectiveness of treatment with that analog. However, imaging with FDG is still important in these patients.

When imaging patients with NETs or prostate tumors, the theranostic tracer (DOTATATE or PMSA) provides high sensitivity for well-differentiated tumors, and tumor uptake predicts response to targeted radionuclide therapy (using Lu177-DOTATATE or Lu177-PSMA, respectively). On the other hand, FDG provides higher sensitivity for poorly-differentiated and higher grade tumors, and uptake of FDG may contraindicate the targeted radionuclide therapies. Combined dual-tracer imaging would thus provide optimal performance, improving sensitivity and staging over either tracer alone, and improve grading by comparing the relative uptake of the two tracers (well-differentiated tumors will have high DOTATATE/PSMA uptake and low FDG update; and vice versa for poorly-differentiated, high-grade tumors). It would also provide a more powerful means of predicting response to targeted radionuclide therapy (DOTATATE/PSMA uptake predicts response, but FDG uptake is a contraindication—and different tumors sites may have different update ratios in the same patient). As such, combined imaging of FDG+DOTATATE or FDG+PSMA would bring significant clinical benefit for these tumor types.

In addition to the preceding example, multi-tracer imaging of numerous other combinations of PET tracers would bring similar benefits for a wide range of diseases and conditions. The ability to perform rapid, efficient, and cost-effective imaging of multiple PET tracers represents an immediate and growing clinical need.

Using current techniques, imaging two PET tracers in the same patient requires that separate scans be performed many hours apart—usually on separate days—to allow for radioactive decay of the first tracer before imaging the second. For example, obtaining FDG & DOTATATE or FDG & PSMA images in a given patient currently requires that separate scans be performed on separate days. This requires the patient to visit the imaging center twice (particularly burdensome for patients who must travel to reach the clinic), repeat pre-scan procedures, and undergo separate PET exams—each with its own CT component and associated radiation exposure. The biggest obstacles blocking routine use of multi-tracer PET are the time, logistical challenges, cost, and undue patient burden associated with bringing a patient back for separate PET scans on separate days-especially considering that they also typically undergo other diagnostic procedures in the short time window before starting treatment.

It is known that dual-tracer PET of certain tracer pairs can be performed where one of the two PET tracers emits a "prompt gamma" (i.e., one of the tracers emits a gamma-ray photon at the same time as the positron emission). By modifying the PET scanner to also detect the prompt gamma, this provides a means to identify counts which have a prompt gamma (i.e. they came from the tracer that emits the gamma) vs. not (i.e. they came from the other tracer). However, this approach has a number of disadvantages, including need for modification of the scanner and limitation to only tracer pairs where one of the two emits a prompt gamma.

These obstacles to acquiring PET scans of multiple tracers in the same patient would be overcome if multiple PET tracers could be imaged simultaneously in a single PET scan, and without any requirement for modification of the scanner or limitation in tracer types other than requiring that each tracer have a different radioactive decay constant.

SUMMARY OF THE INVENTION

An object of the present invention is to enable simultaneous multi-tracer PET imaging with two or more tracers to be routinely performed in a single scanning session with reasonable scan times, such as scan times of 30-60 minutes or less.

Another object of the present invention is to enable multi-tracer PET to be routinely performed, providing accurate images of each tracer recovered from the multi-tracer scans.

Another object of the present invention is to provide a system and method (e.g., a medical device and associated processes) for simultaneous multi-tracer PET imaging of a variety of tracer combinations.

Another object of the present invention is to provide a system and method for recovering individual-tracer results from simultaneous multi-tracer PET data that addresses noise sensitivity and accounts for ongoing tracer kinetics.

In embodiments, the multi-tracer PET is dual-tracer PET.

A method is provided comprising:
A) receiving, at one or more computers, digital data generated by positron emission tomography (PET) scans of a region of interest of a physiologic body which has been administered at least two PET tracers that differ from one another at least in their radioactive decay constant, the digital data comprising PET information associated with at least two time points, the at least two time points obtained after the administration of the at least two PET tracers and subsequent to initial wash-in phase of distribution throughout the body; and
B) determining, by the one or more computers, based on the radioactive decay constants of each PET tracer, at least one set of output digital data, the at least one set of output digital data corresponding to at least one of the at least two PET tracers, the step of determining comprising at least one of the following sub-steps:
  i. regularizing to account for statistical noise;
  ii. preconditioning the digital data to be more amenable to signal separation;
  iii. applying feature preservation techniques; or
  iv. accounting for late tracer kinetics.

In embodiments, the method further comprises generating, by the one or more computers, at least one image based on the determined at least one set of output digital data, the at least one image indicating PET tracer data within the region of interest for a respective one of the at least two PET tracers associated with the at least two time points.

In embodiments, the step of generating comprises generating at least two images, each of the at least two images corresponding to the at least one set of output digital data.

In embodiments, the at least two images are static images.

In embodiments, the at least two images are dynamic images.

In embodiments, the at least two images comprise a static image and a dynamic image.

In embodiments, the at least two images are decay corrected.

In embodiments, a kinetic factor for at least one of the at least two PET tracers is allowed to differ from the known radioactive decay constant in order to account for late tracer kinetics.

In embodiments, the kinetic factor for at least one of the at least two PET tracers is constrained to be equal to or larger than that tracer's known radioactive decay constant.

In embodiments, the kinetic factor for at least one of the at least two PET tracers is constrained to be equal to or smaller than that tracer's known radioactive decay constant.

In embodiments, the kinetic factor for at least one of the at least two PET tracers is constrained to be equal to or larger than that tracer's known radioactive decay constant, and the kinetic factor for at least one other PET tracer is constrained to be less than or equal to that tracer's known radioactive decay constant.

In embodiments, the method further comprises, at a time subsequent to step A), a step of co-registering the image data over the at least two time points to correct for patient motion.

In embodiments, in B) determining is performed independently for each set of received digital data.

In embodiments, the region of interest comprises a voxel.

In embodiments, the region of interest comprises a plurality of voxels.

In embodiments, the digital data comprises tracer activity, tracer activity concentration, or tracer uptake.

In embodiments, in B), at least two sets of output data are determined, each of the at least two sets of output data corresponding to a different tracer.

In embodiments, the method further comprises generating, by the one or more computers, at least two images based on the determined at least two sets of output digital data, the at least two images indicating PET tracer data within the region of interest for the at least two PET tracers associated with the at least two time points.

In embodiments, the digital data comprises a PET image comprising a set of voxel data.

In embodiments, the digital data comprises at least one region of a PET image.

In embodiments, the digital data comprises at least one value representing at least one region of a PET image (i.e., ROI data).

In embodiments, the digital data comprises PET listmode data.

In embodiments, the digital data comprises PET sinogram data.

In embodiments, B) comprises separate steps of determining factors representing relative contribution of at least one of the at least two PET tracers, and then applying the factors to the received digital data to determine the at least one set of output digital data.

In embodiments, B)i) comprises a finite impulse response filter.

In embodiments, B)i) comprises a median filter.

In embodiments, B)i) comprises regularization using component-analysis methods.

In embodiments, B)ii) comprises transforming the received digital data into components before determining the output digital data.

In embodiments, B)iii) comprises transforming the received digital data into components and constraining a summed contribution of at least one component of the output data over all tracers to match a contribution of the at least one component in the received digital data.

In embodiments, B)iii) comprises decomposing the received digital data into a set of features and applying a constraint that features which are not present in the received digital data are not allowed to be present in the output digital data.

In embodiments, B)iii) comprises decomposing the received digital data into a set of features and applying a constraint that a magnitude of at least one feature in the output digital data cannot be larger than a magnitude of the feature in the received digital data.

In embodiments, B)iii) comprises structure-based decomposition in which image structure information contained in the received digital data is preserved in the output digital data.

In embodiments, only two PET tracers are employed.

In embodiments, one tracer of the at least two PET tracers is F18-Fluorodeoxyglucose.

In embodiments, another tracer of the at least two PET tracers images prostate-specific membrane antigen (PSMA) expression.

In embodiments, at least one tracer of the at least two PET tracers images prostate-specific membrane antigen (PSMA) expression.

In embodiments, the tracer that images prostate-specific membrane antigen (PSMA) expression comprises a tracer selected from the listing consisting of: Ga68-labeled PSMA ligands, Ga68-PSMA-11, Ga68-PSMA-617, Ga68-PSMA-I&T, F18-piflufloflastat, F18-flotufolastat, F18-PSMA-1007, and F18-fluciclovine.

In embodiments, at least one tracer of the at least two PET tracers images somatostatin receptor (SSTR) expressing tumors.

In embodiments, the tracer that images SSTR comprises a tracer selected from the group consisting of: Ga68-DOTATATE, Ga68-DOTATOC, Ga68-DOTANOC, Cu64-DOTATATE, Gluc-Lys-[F18]FP-TOCA, [F18]F-FET-BAG-TOCA, [F18|AIF-NOTA-Octreotide, [A118F]NODA-MPAA-HTA, [18F]SiTATE, and | 18F]AIF-NOTA-JR11.

In embodiments, at least one tracer of the at least two PET tracers images myocardial perfusion, viability, metabolism, or inflammation.

In embodiments, the tracer that images myocardial perfusion, viability, metabolism, or inflammation comprises a tracer selected from the group consisting of: Rb82, N13-ammonia, O15-water, F18-flurpiridaz, F18-fluorodeoxyglucose, F18-FDHR, F18-FBnTP, F18-FTPP, F18-RP1004, F18-FP2OP, F18-FTHA, F18-FTP, F18-FTO, Cu62-PTSM, Cu64-PTSM, Cu62-ATSM, Cu64-ATSM. Ga68-BAPEN, C11-acetate, C11-acetyl-CoA, C11-palmitate.

In embodiments, at least one tracer of the at least two PET tracers image is used for imaging dementia, including tracers for misfolded proteins, neuroinflammation, elements of the cholinergic system, elements of monoamine neurotransmitter systems, synaptic density, cerebral energy metabolism, and various other proteins.

In embodiments, at least one tracer of the at least two PET tracers is a radiolabeled monoclonal antibody.

In embodiments, at least one tracer of the at least two PET tracers is used for imaging bone and areas of osteogenic activity.

In embodiments, at least one tracer of the at least two PET tracers images inflammation or inflammatory processes.

In embodiments, at least one tracer of the at least two PET tracers images sarcoidosis.

In embodiments, one tracer of the at least two PET tracers is:
   [15O] Water
   [13N] Ammonia
   [82Rb] Rubidium-82 chloride
   [11C] Acetate
   [$^{11}$C] 25B-NBOMe (Cimbi-36)
   [$^{18}$F] Altanserin
   [$^{11}$C] Carfentanil
   [$^{11}$C] Choline
   [$^{11}$C] DASB
   [$^{11}$C] DTBZor [$^{18}$F]Fluoropropyl-DTBZ
   [$^{18}$F] Fallypride
   [$^{18}$F] Florbetaben
   [$^{18}$F] Florbetapir
   [$^{18}$F] Flortaucipir
   [$^{18}$F] Flubatine
   [$^{18}$F] Flotufolastat
   [$^{18}$F] or [$^{11}$C] Flumazenil
   [$^{18}$F] Flurpiridaz
   [$^{18}$F] Fluspidine
   [$^{18}$F] Flutemetamol
   [$^{18}$F] Fluorodopa
   [$^{18}$F] Desmethoxyfallypride
   [$^{18}$F] Mefway
   [$^{18}$F] MPPF
   [$^{18}$F] Nifene
   [$^{11}$C] Pittsburgh compound B
   [$^{11}$C] Raclopride
   [$^{18}$F] Setoperone
   [$^{18}$F] or [$^{11}$C] N-Methylspiperone
   [$^{11}$C] Verapamil
   [$^{11}$C] Martinostat
   [$^{11}$C] Acetate
   [$^{11}$C] Acetyl COA
   [$^{11}$C] Palmitate
   [$^{11}$C] Methionine
   [$^{11}$C] Choline
   [$^{11}$C] Glucose
   [$^{18}$F] EF5
   [$^{18}$F] Fluciclovine
   [$^{18}$F] Fluorocholine
   [$^{18}$F] Fluoroestradiol
   [$^{18}$F] FET
   [$^{18}$F] FMISO
   [$^{18}$F] Fluorothymidine
   [$^{18}$F] Piflufolastat
   [$^{18}$F] Sodium Fluoride
   [$^{18}$F] Octreotide
   [$^{64}$Cu] Cu-ETS
   [$^{62}$Cu] Cu-ATSM
   [$^{64}$Cu] Cu-ATSM
   [$^{62}$Cu] Cu-PTSM
   [$^{64}$Cu] Cu-PTSM
   [$^{64}$Cu] DOTATATE
   [68Ga] DOTA-pseudopeptides
   [68Ga] DOTATATE
   [68Ga] DOTATOC
   [68Ga] DOTANOC
   [68Ga] Gozetotide
   [68Ga] PSMA
   [68Ga] CXCR4; or
   [$^{18}$F] Fluorodeoxysorbitol (FDS).

A method of diagnosing a cancer in a subject comprising detecting or characterizing one or more lesions in a subject by a PET scan employing two PET tracers using a method described herein.

A method of guiding selection of therapy or predicting response to therapy in a subject with at least one malignant tumor comprising evaluating tumor uptake of at least two tracers by a PET scan employing the at least two PET tracers using a method described herein.

A method of monitoring the progress of at least one round of treatment in a subject with at least one malignant tumor comprising assessing the function of the at least one tumor in a subject by a first PET scan before the at least one round of said treatment, and at least a second PET scan after the at least one round of said treatment, with at least one of the said PET scans employing at least two PET tracers using a method described herein, and comparing therefrom the difference in the at least one tracer's uptake in the at least one tumor before and after said treatment, so as to monitor the progress of the treatment.

A method of diagnosing a cardiac condition in a subject comprising identifying the presence of a cardiac condition in a subject by a PET scan employing two PET tracers using a method described herein.

A method of diagnosing or assessing coronary artery disease in a subject comprising assessing myocardial blood flow at rest and at stress by employing two PET tracers using a method described herein.

A method of diagnosing or assessing coronary artery disease in a subject comprising assessing myocardial blood flow and myocardial viability by employing two PET tracers using a method described herein.

A method of diagnosing or assessing coronary artery disease in a subject comprising assessing myocardial blood flow at rest, myocardial blood flow and at stress, and myocardial viability by employing three PET tracers using a method described herein.

A method of monitoring the progress of a treatment of a cardiac condition in a subject comprising assessing the severity or extent of the cardiac condition in a subject after said treatment by a PET scan employing two PET tracers using a method described herein.

A method of monitoring the progress of a treatment of a cardiac condition in a subject comprising assessing the severity or extent of the cardiac condition in a subject before and after said treatment by a first PET scan before and a second PET scan after said treatment, at least one of the said PET scans employing at least PET tracers using a method described herein, and comparing therefrom the severity or extent of the cardiac condition in a subject before and after said treatment, so as to monitor the progress of the treatment.

A method of diagnosing a neurological condition in a subject comprising detecting or characterizing the neurological condition in a subject by a PET scan employing two PET tracers using a method described herein.

A method of monitoring the progress of a treatment on a neurological condition in a subject comprising assessing the severity or extent of the neurological condition in a subject before and after said treatment by a PET scan before and after said treatment, each PET scan employing two PET tracers using a method described herein, and comparing therefrom the severity or extent of the neurological condition in a subject before and after said treatment, so as to monitor the progress of the treatment.

A method of performing a simultaneous multi-PET tracer scan on a subject comprising administering to the subject or having administered to the subject, the multiple PET tracers and performing simultaneous multi-tracer PET imaging of a portion of said subject using a method disclosed herein. In embodiments, the simultaneous multi-PET tracer scan is a simultaneous dual-PET tracer scan.

A system comprising:
one or more processors; and
a non-transitory computer readable memory operatively connected to the one or more processors and containing instructions stored thereon for the one or more processors to carry out a process comprising:
A) receiving, at one or more computers, digital data generated by positron emission tomography (PET) scans of a region of interest of a physiologic body which has been administered at least two PET tracers that differ from one another at least in their radioactive decay constant, the digital data comprising PET information associated with at least two time points, the at least two time points obtained after the administration of the at least two PET tracers and subsequent to initial wash-in phase of distribution throughout the body;
B) determining, by the one or more computers, based on the radioactive decay constants of each PET tracer, at least one set of output digital data, the at least one set of output digital data corresponding to at least one of the at least two PET tracers, the step of determining comprising at least one of the following sub-steps:
 i. regularizing to account for statistical noise; or
 ii. preconditioning the digital data to be more amenable to signal separation;
 iii. applying feature preservation techniques;
 iv. accounting for late tracer kinetics.

BRIEF DESCRIPTION OF THE DRAWINGS

The above and related objects, features and advantages of the present invention will be more fully understood by reference to the following detail description of the exemplary, albeit illustrative, embodiments of the present invention in conjunction with the accompanying figures, wherein:

FIG. 3A is a flowchart depicting a process in accordance with an exemplary embodiment of the present invention where two regularization steps are applied before computing signal-separation factors;

FIG. 3B is a flowchart depicting a process in accordance with an exemplary embodiment of the present invention in which preconditioning is applied by transforming received dual-tracer PET image into principal components, regularization is applied to the, and then signal separation factors are determined for each component;

FIG. 3C is a flowchart depicting a process in accordance with an exemplary embodiment of the present invention in which feature preservation is applied with regularization, and signal-separation factors are computed for each feature;

DETAILED DESCRIPTION

Preferred Embodiments

Figure 1A:
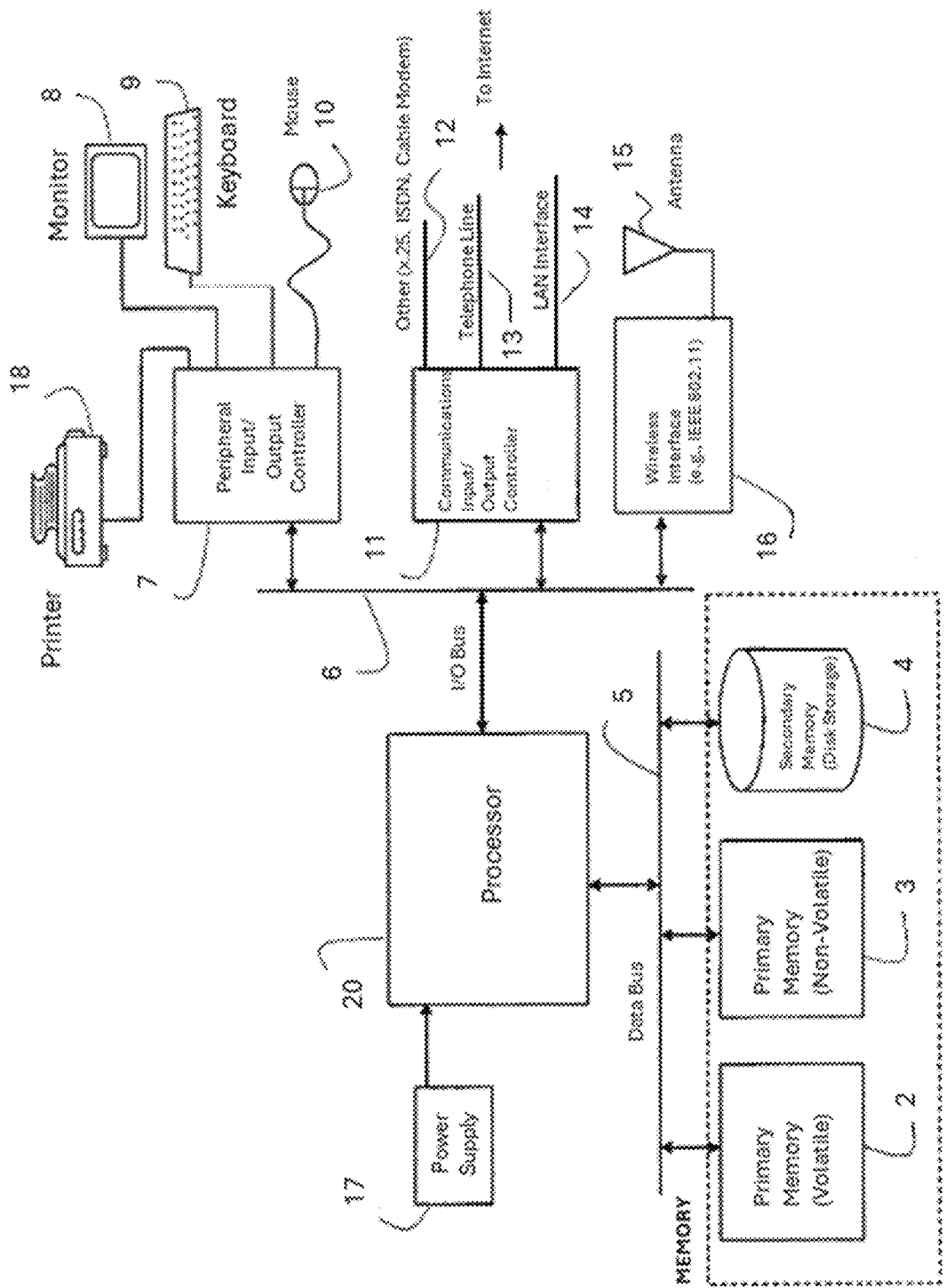
FIGS. 1A and 1B are block diagrams of a computer system that may be used to carry out the processes of various exemplary embodiments of the present invention.

As used herein, the term PET "signal" is broadly used to describe the essence of the PET measurement under discussion. The term "multi-tracer" is used to denote simultaneous imaging of two or more tracers, and the term "dual-tracer" is used for specific examples involving two tracers, without restricting generality to more than two tracers. "Signal separation" (and "signal recovery") refer to the process of separating a multi-tracer dataset and recovering at least one individual tracer component, thereby recovering the necessary signal for one or more individual tracers for computing the desired endpoint. To varying degrees multi-tracer PET signal separation can be performed on the raw scanner data, partially processed data, reconstructed images, image regions, and/or time-activity curves; similarly, for each tracer, the imaging endpoint(s) may be a static image, standardized uptake value (SUV), pseudo-quantitative measure, dynamic image, kinetic parameter(s) and/or macro parameter(s). For a given dataset and imaging endpoint, "signal" is used to identify the element or elements of the dataset necessary for computing the desired endpoint.

As will be appreciated by one skilled in the art, the preferred embodiment may be implemented as a method, a data processing system, or a computer program product. Accordingly, the preferred embodiment may take the form of an entirely hardware embodiment, an entirely software embodiment, or an embodiment combining software and hardware aspects. Furthermore, implementations of the preferred embodiment may take the form of a computer program product on a computer-readable storage medium having computer-readable program instructions (e.g., computer software) embodied in the storage medium. More particularly, implementations of the preferred embodiments may take the form of web-implemented computer software. Any suitable computer-readable storage medium may be utilized including hard disks, CD-ROMs, optical storage devices, or magnetic storage devices.

The preferred embodiments according to the present invention are described below with reference to block diagrams and flowchart illustrations of methods, apparatuses (i.e., systems) and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In the embodiments referenced herein, a "computer" or "computing device" may be referenced. Such computer may be, for example, a mainframe, desktop, notebook or laptop, a hand held device such as a data acquisition and storage device, or it may be a processing device embodied within another apparatus such as, for example, a scanner used for tomography. In some instances the computer may be a terminal used to access data or processors over a network. Turning to FIG. 1a, one embodiment of a computing system 1 is illustrated that can be used to practice aspects of the preferred embodiment. In FIG. 1 a, a processor 20, such as a microprocessor, is used to execute software instructions for carrying out the defined steps. The processor 20 receives power from a power supply 17 that also provides power to the other components as necessary. The processor 20 communicates using a data bus 5 that may be 16 or 32 bits wide (e.g., in parallel). The data bus 5 is used to convey data and program instructions, typically, between the processor and memory. In the present embodiment, memory can be considered primary memory 2 that is RAM or other forms which retain the contents only during operation, or it may be non-volatile 3, such as ROM, EPROM, EEPROM, FLASH, or other types of memory that retain the memory contents at all times. The memory could also be secondary memory 4, such as disk storage, that stores large amount of data. In some embodiments, the disk storage may communicate with the processor using an I/O bus 6 instead or a dedicated bus (not shown). The secondary memory may be a floppy disk, hard disk, compact disk, DVD, or any other type of mass storage type known to those skilled in the computer arts.

The processor 20 also communicates with various peripherals or external devices using an I/O bus 6. In the present embodiment, a peripheral I/O controller 7 is used to provide standard interfaces, such as RS-232, RS422, DIN, USB, or other interfaces as appropriate to interface various input/output devices. Typical input/output devices include local printers 18, a monitor 8, a keyboard 9, and a mouse 10 or other typical pointing devices (e.g., rollerball, trackpad, joystick, etc.).

The processor 20 typically also communicates using a communications I/O controller 11 with external communication networks, and may use a variety of interfaces such as data communication oriented protocols 12 such as X.25, ISDN, DSL, cable modems, etc. The communications controller 11 may also incorporate a modem (not shown) for interfacing and communicating with a standard telephone line 13. Finally, the communications I/O controller may incorporate an Ethernet interface 14 for communicating over a LAN. Any of these interfaces may be used to access a wide area network such as the Internet, intranets, LANs, or other data communication facilities.

Finally, the processor 20 may communicate with a wireless interface 16 that is operatively connected to an antenna 15 for communicating wirelessly with another device, using for example, one of the IEEE 802.11 protocols, 802.15.4 protocol, or a standard 3G wireless telecommunications protocols, such as CDMA2000 1× EV-DO, GPRS, W-CDMA, or other protocol.

Figure 1B:
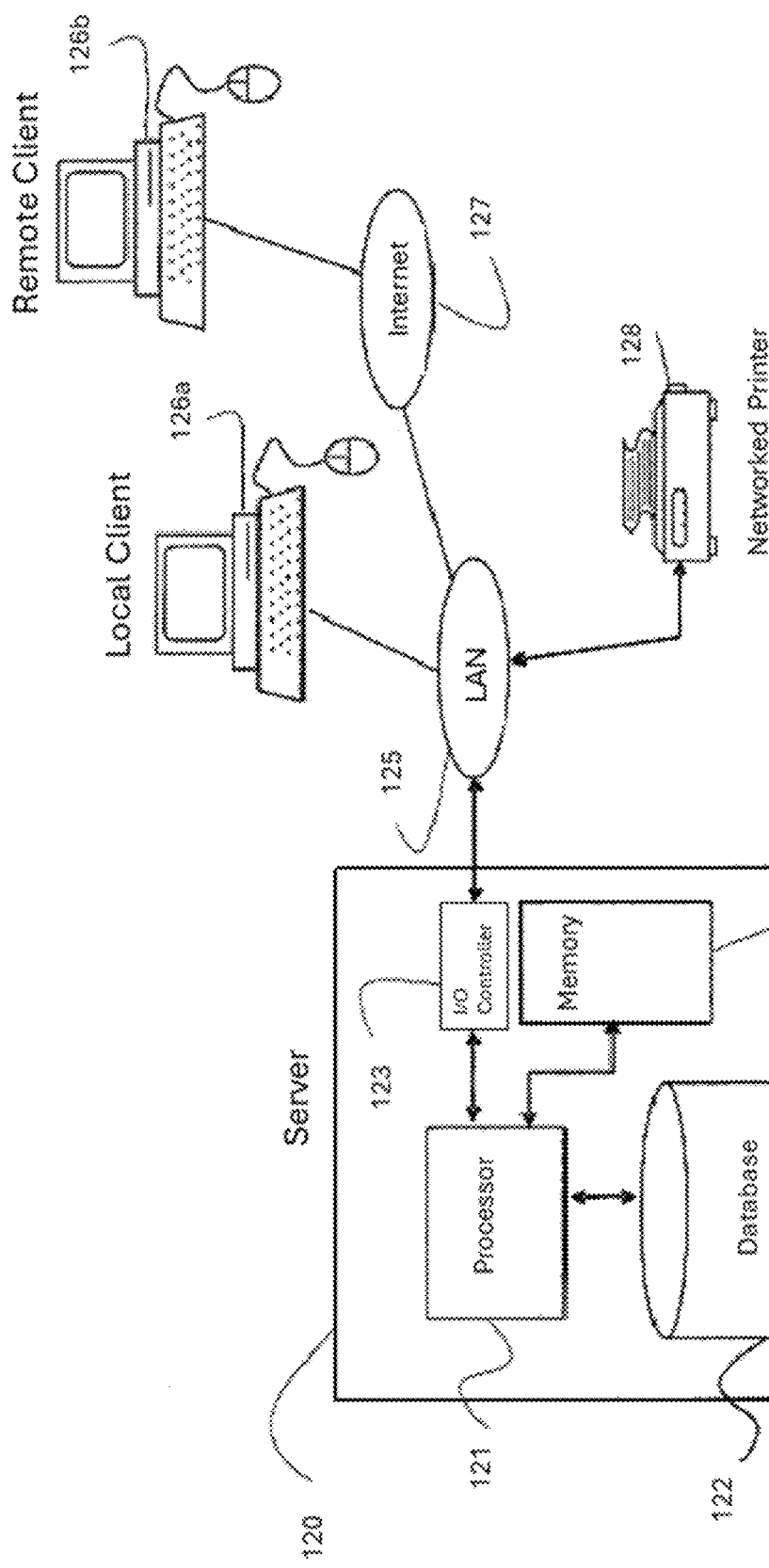

An alternative embodiment of a processing system that may be used is shown in FIG. 1b. In this embodiment, a distributed communication and processing architecture is shown involving a server 120 communicating with either a local client computer 126 a or a remote client computer 120b. The server 120 typically comprises a processor 121 that communicates with a database 122, which can be viewed as a form of secondary memory, as well as primary memory 124. The processor also communicates with external devices using an I/O controller 123 that typically interfaces with a LAN 125. The LAN may provide local connectivity to a networked printer 128 and the local client computer 126a. These may be located in the same facility as the server, though not necessarily in the same room. Communication with remote devices typically is accomplished by routing data from the LAN 125 over a communications facility to a wide area network 127, such as the Internet. A remote client computer 126b may execute a web browser, so that the remote client 126b may interact with the server as required by transmitted data through the wide area network 127, over the LAN 125, and to the server 120.

Those skilled in the art of data networking will realize that many other alternatives and architectures are possible and can be used to practice the preferred embodiments. The embodiments illustrated in FIGS. 1a and 1b can be modified in different ways and be within the scope of the present invention as claimed.

In exemplary embodiments, systems and methods of the present invention may be implemented using adapted software products, such as, for example, mfiVerse™ (Multi-Functional Imaging LLC (MFI), South Ogden, Utah, USA) as modified with additional capabilities to carry out the processes described herein. The systems and processes of the non-adapted mfiVerse™ software are covered at least under U.S. Pat. Nos. 7,848,557 and 10,175,216, the contents of which are incorporated herein by reference in their entirety.

The methods of U.S. Pat. No. 7,848,557 are applicable to multi-tracer PET data wherein PET scan data is acquired concurrently or subsequent to administration of a first PET tracer, and continues during administration of a second PET tracer and for at least a portion of time after introduction of the second tracer. In other words, the PET scan is acquired during the administration of the second PET tracer (and often during the administration of the first PET tracer as well). The kinetic model used in that method must account for the initial uptake and distribution "wash-in" phase of the second tracer (as also the wash-in phase of the first tracer, in cases where the PET scan covers administration of the first tracer as well); in addition, the kinetics of this tracer wash-in phase provide the primary source of information for separating and recovering the signals for each tracer. This differs from the present invention, wherein the PET scan commences after all PET tracers are administered and after the initial uptake and distribution "wash-in" phase is complete. As such, the kinetic distribution of the tracers for the present invention is largely (but not completely) fixed, and only small and/or slow changes in distribution remain. Notably, these "late tracer kinetics" do not provide sufficient information for separating and recovering the individual-tracer signals as done in U.S. Pat. No. 7,848,557; rather, the current invention uses differences in radioactive decay constant for each tracer to separate and recover the individual-tracer signals.

U.S. Pat. No. 10,175,216 covers systems and methods for fitting kinetic models to dynamic medical imaging data. These methods may be applied to single-tracer data as well as to multi-tracer data, and they compute fitted kinetic model parameters and curves. However, these methods do not provide a means for separating and recovering individual-tracer signals from multi-tracer data. The methods of U.S. Pat. No. 10,175,216 provide one way of performing the kinetic model fits that may be performed when using the methods of U.S. Pat. No. 7,848,557 or for the present invention; however, the methods of U.S. Pat. No. 10,175, 216 are distinct in that they are methods for fitting kinetic models and not methods for separating multi-tracer data.

The present invention receives and processes digital data from multi-tracer PET scans using differences in radioactive decay for each tracer to separate and recover individual-tracer signals from the multi-tracer data, where the processed data may be used to generate at least one image indicating PET tracer data corresponding to at least one of the multiple tracers. In 1982 Huang et al published a paper (J Nucl Med 23:816-822, 1982) describing a dual-tracer technique for positron computerized tomography (PCT) where differences in physical decay rates were used to distinguish between two positron emitters. The technique showed potential for imaging two positron emitters with PCT, for measuring photon attenuation, and reducing patient motion artifacts. The technique was found to have high noise sensitivity that was problematic, and it was only applied to plastic-and-water phantoms where the tracers were fully fixed and did not experience any distribution kinetics during imaging. Although this work was published 4 decades ago, the technique is not in use today due to these technological challenges. The present invention overcomes these challenges by using image co-registration, regularization, pre-conditioning, and feature preservation techniques to overcome the problematic noise sensitivity inherent in decay-based signal-separation, plus methods that account for late tracer kinetics and enable simultaneous multi-tracer PET to be performed in patients where tracer activity distributions are never fully fixed.

Benefits of Multi-Tracer Scanning

The ability to image multiple tracers in a single PET/CT exam greatly improves the patient experience, requires only a single trip to the imaging center, simplifies scheduling demands, and reduces overhead. It also reduces technologist workload because the patient would only need to be positioned once, and only one CT scan would be needed for PET attenuation correction (thereby reducing radiation exposure to the patient). In addition, the images would be 'natively' co-registered since the patient remains motionless or at least close to motionless on the imaging table for all scans (frame-by-frame image co-registration may still be required in the event of patient motion while scanning). Simultaneous multi-tracer imaging would also benefit the imaging clinic by greatly increasing throughput and improving utilization of the PET/CT scanner resource. While simultaneous dual-tracer PET based on differences in radioactive decay was first proposed in 1982, the technique has never before been translated to a working, practicable approach. High noise sensitivity and ongoing tracer kinetic changes that occur during the PET scan have previously been insurmountable technological challenges.

Testing with Synthesized Data

One challenge of developing and evaluating rapid multi-tracer PET techniques is the need to know the ground truth when evaluating results. For example, to evaluate a given dual-tracer combination, one possible technique would be to obtain separate, single-tracer scans with each tracer on separate days, and then to obtain simultaneous multi-tracer scans on a $3^{rd}$ day—all in the same patient. Here the separate-scan images of each tracer could be used as the standard for evaluating images of each tracer recovered from the dual-tracer scans. However, such an approach would pose many problems, in particular: (1) high cost, scheduling challenges, and patient compliance issues for performing three different PET/CT exams on three different days; (2) increased radiation exposure from three PET/CT exams (3 CTs and 4 total PET tracer administrations); and (3) test-retest variability for PET is on the order of 10-15%—differences that can be much larger than the errors in recovered dual-tracer images and thus limit the value of this technique.

In accordance with exemplary embodiments of the present invention, separate, single-tracer PET scans with each tracer are acquired, and then the images are combined to "synthesize" dual-tracer images which are almost (but not quite) identical to the images that would have been obtained from actual dual-tracer scanning. The approach involves three steps: • Step 1) Co-register the separately-acquired single-tracer scan images from each patient using both manual and semi-automated techniques (rigid and non-rigid body transformations). The co-registration involves frame-by-frame co-registration feature(s) to be developed as part of the signal separation algorithms as described below • Step 2) Add the co-registered reconstructed images for each time-point to create "synthesized" dual-tracer images. When two PET tracers are present during a scan, the measured data is essentially the sum of the data that would be measured for each tracer individually. Differences from actual dual-tracer scans include differences in count-rates (and hence dead-time), randoms, and slight differences in positron range; however, these processes are well understood and accurately corrected by modern PET tomographs. • Step 3) The original single-tracer images provide the ground truth for evaluating recovery of individual-tracer images from the synthesized dual-tracer datasets-in effect, the data act as their own controls. These evaluations test how well the signal separation algorithms can recover individual-tracer images that are identical (or substantially equivalent) to images obtained from separate, single-tracer scanning. Note also that this approach "pairs" the noise in the single- and dual-tracer images, permitting paired sampling tests to be used (substantially increasing the statistical power as compared to un-paired tests). Other advantages of the technique include the ability to scale each tracer's image before combining them in order to simulate changing the administered activity of each tracer. While this does not directly account for differences in statistical noise that would arise from actual changes in administered activity, it does provide a reasonable and efficient approach for characterizing the effect of changing the relative administered dose of the two tracers.

EXEMPLARY EMBODIMENTS

Figure 2:
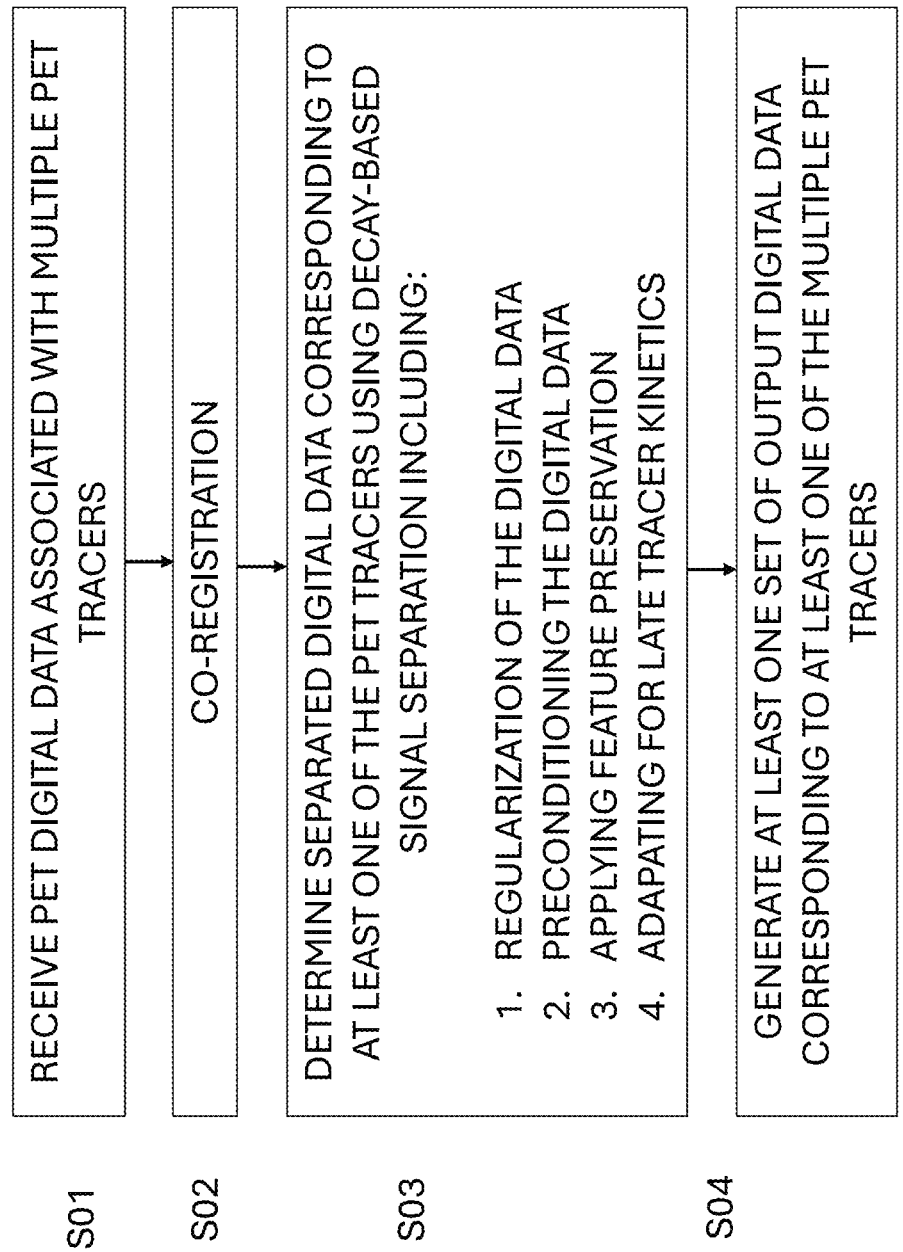
FIG. 2 is a flowchart showing a method of multi-tracer signal separation according to an exemplary embodiment of the present invention.

FIG. 2 is a flowchart showing a method of multi-tracer signal separation according to an exemplary embodiment of the present invention. In step S01 of the process, the system, the system receives digital data generated by PET scans of a region of interest of a physiologic body which has been administered at least two PET tracers that differ from one another at least in their radioactive decay constant, where the digital data includes PET information associated with at least two time points that occur at times after administration of the at least two PET tracers and subsequent to the initial wash-in phase of tracer uptake and distribution throughout the body. The region of interest may be, for example, a voxel or a plurality of voxels covering a local region of the body or the entire patient. The digital data may correspond to and/or contain information associated with, for example, tracer activity or uptake, a PET image comprising a set of voxel data, at least one region of a PET image, at least one value representing at least one region of a PET image (i.e. ROI data), PET listmode data, and/or PET sinogram data. In exemplary embodiments, the digital data may include first PET information associated with a first point in time and second PET information associated with at least a second point in time. Each tracer may be administered simultaneously, concurrently (one after the other), or separately at different points in time, before the imaging occurs.

In order to perform signal separation and recover output data for each component tracer, it is important to ensure that the received digital data are accurately co-registered for each timepoint; otherwise, misregistration of image structures may produce biased results. Tracer distributions underlying each frame are either fixed or slowly varying (1 hr or longer after tracer administration), and thus image features and landmarks are very similar for each timepoint. This co-registration problem is much simpler than, for example, aligning PET and CT images, which have very different image features. Also, since the patient remains on the scanner for each whole-body pass (without getting up), any mis-registrations will be due to patient motion and not to (much larger) differences in patient positioning.

In exemplary embodiments, the process includes step S02 of co-registering the images at each time point. This step may be performed using manual, semi-automated, or fully-automated image co-registration tools. For example, software packages such as Automatic Image Reconstruction (AIR) tool (Laboratory of Neuro Imaging, University of Southern California) or the Elastix image registration toolbox built upon the Insight Segmentation and Registration Toolkit (ITK; Insight Software Consortium) provide tools for a wide range of image co-registration techniques. Those skilled in the art of image co-registration will realize that many other tools or approaches may be used to perform image co-registration. For the present invention, the images at each time point are very similar, coming from scans of the patient and different points in time. As such, the image characteristics and features at each time point are closely related, differing in radioactive decay of the tracers plus any late ongoing tracer kinetic changes. This image co-registration step is much simpler than, say, co-registering images from different modalities where the image characteristics and features may widely differ. If no patient motion has occurred between the different time points, then image co-registration may not be needed; however, proper alignment of the images for each time point should be assured before going beyond step S02.

In step S03 of the process, the system processes the received digital data to determine separate sets of output digital data, each associated with an individual tracer. In exemplary embodiments, separation is based on differences in radioactive decay of the tracer pairs. If two tracers are present, under the assumption that each tracer's distribution is fixed during the PET scans, the PET signal for a given voxel or individual region can be written as follows:

$$r(t) = A_1 e^{-\lambda_1 t} + A_2 e^{-\lambda_2 t} \tag{1}$$

where,
r(t)=PET signal at time t
$A_k$=fixed activity for tracer k
$\lambda_k$=radioactive decay constant for tracer k
t=time.

Measuring multiple timepoints gives sets of equations for all measured timepoints n as follows:

$$R_n = A_1 e^{-\lambda_1 t_n} + A_2 e^{-\lambda_2 t_n} \tag{2}$$

Eq. 2 is easily solved to recover the individual-tracer activities $A_1$ and $A_2$ for tracer 1 and tracer 2, respectively. The radioactive decay constants $\lambda$ are known a priori.

If more than two tracers are present, then additional terms are included in the sum for each tracer. When the received digital data comprises a plurality of locations, such as a set of voxels that form an image, then Eqs. 1 and 2 are repeated for each voxel or location, and individual-tracer activities $A_k$ are recovered for each voxel or location. The group of recovered individual-tracer activities over all voxels or locations forms an image of each tracer.

The recovery of $A_k$ for each tracer k is a signal separation process, as it decomposes the multi-tracer PET signal into individual-tracer components. In some exemplary embodiments, the values of $A_k$ are used directly to form the output digital data for each tracer. In other exemplary embodiments, however, the values of $A_k$ are intermediate separated data, and additional processing steps are performed using these data in order to form the output digital data.

In exemplary embodiments, to account for statistical noise and any ongoing tracer kinetics, step S03 also involves enhancement and/or optimization of the signal separation algorithm. For example, step S03 includes one or more of the following sub-processes: regularizing to mitigate the effects of statistical noise; preconditioning the digital data to make it more amenable to signal separation; applying feature preservation techniques to ensure accurate recover of individual tracer features; and accounting for late tracer kinetics. These sub-processes are not all fully distinct and may share some characteristics: for example, preconditioning and feature preservation may both also have a regularizing effect on the data. Each of these sub-processes are described below.

Regularization (S03-1)

Regularization is the process of modifying a signal, such as a set of digital data or image, to reduce the effects of noise or other perturbations that can affect the quality of the signal or of operations performed on the signal. Regularization is also known by a variety of other terms, such as apodization or de-noising. Regularization can be applied directly to a dataset, for example by applying low-pass or smoothing filters, or within processing algorithms, such as by adding constraints or penalty terms that suppress frequencies dominated by noise.

In exemplary embodiments, regularization may be applied to the digital data before signal separation processing in order to reduce the effects of statistical noise. Consider a single dual-tracer image voxel measured over multiple timepoints. If both tracers are static and there is no noise, then the voxel values will exactly match the dual-tracer decay model: $R(n) = A_1 e^{-\lambda_1 m} + A_2 e^{-\lambda_2 m}$. However, when noise is present, each value $R(n)$ will differ from the mean (true) value by some noise $\Delta(n)$, and resultant estimates for $A_1$ and $A_2$ will be affected by this noise. Note that while the sum $A_1 + A_2$ may be fairly insensitive to noise because this is the "DC" term of fit, the individual values of $A_1$ and $A_2$ may be very sensitive to noise because a small overestimation of $A_1$ can be offset by an underestimation of $A_2$. In other words, the estimated values of $A_1$ and $A_2$ will be strongly negatively correlated. This is a main underlying cause of high noise sensitivity of "naïve" decay-based signal separation.

In order to reduce the effects of noise, the data $R(n)$ may be regularized before processing, for example by applying a low-pass finite impulse response (FIR) filter or convolving with a smoothing kernel such as a Gaussian. The has the effect of reducing the higher-frequency components of $R(n)$ that are dominated by noise, and thus may improve the accuracy of the multi-tracer signal separation. However, it may also cause a undesirable biases such as loss of spatial resolution or loss of contrast. Differing filtering techniques, such as edge-preserving filters or medial filters, may have offer different noise-suppression vs. bias trade-offs. Depending on the particular application, the benefits of pre-regularizing the digital data before signal separation may outweigh the cost of the associated bias.

In other exemplary embodiments, regularization may be applied during the signal separation processing itself. For example, constraints or penalty terms may be added to the algorithm used to solver Eq. 2. As with filtering the data before signal separation, these approaches may also have a noise vs. bias tradeoff; however, the characteristics of this tradeoff may offer advantages over pre-filtering in some uses.

FIG. 3A shows a flowchart depicting an exemplary embodiment where two regularization steps are applied before computing the signal-separation factors. In step S31 of the process, the system receives a dual-tracer PET image, and then performs regularization on the image, which may include application of an edge-preserving filter (step S33) and/or application of a median filter (step S35). The system then compiles signal separation factors (step S37) with input of late tracer kinetics (step S39), and applies the signal separation factors to the filtered image (step S41). Output images of tracer 1 and tracer 2 are then generated (steps S43 and step S45) based on the separated and filtered images. Those skilled in the art of fitting equations and solving inverse problems will realize that many other regularization approaches are possible and can be used to practice the preferred embodiments.

Pre-Conditioning (S03-2)

Pre-conditioners are mathematical transforms that convert a mathematical problem into a related space where the problem has a lower condition number. In other words, it "conditions" the problem to be less sensitive to statistical noise and other perturbations. The problem is solved in that related space, and the solution is then transformed back to the original space.

In exemplary embodiments of the present invention, through the use of pre-conditioners and careful application to the signal separation algorithm, it is possible to achieve similar reductions in noise sensitivity for the decay-model fits, without blurring the spatial resolution of the output images. In this regard, it is important to apply the pre-conditioners a priori to the images to improve the decay-model fits, but the fit results are then applied to the original (non-conditioned) image in order to preserve its fidelity and that of the recovered output images.

For example, in one such exemplary embodiment copies of the multi-tracer images are pre-filtered to reduce the effects of noise. Signal separation is then applied to the pre-filtered copies in order to obtain factors representing the relative contribution of each individual tracer at each image location. These factors benefit from the regularization of pre-filtering, but they also have a loss of resolution and contrast. Rather than using these factors directly to generate output images, the factors are applied to the original (unfiltered) images, which do not have such a loss of resolution or contrast. As a result, the signal separation process benefits from the noise reduction of pre-filtering, but the bias associated with that regularization has minimal effect on the recovered individual-tracer images. Since the problem of solving Eq. 2 in this embodiment occurs in the regularized space but the signal separation factors are applied in the original space, this is a form of preconditioning.

In other exemplary embodiments, component analysis techniques such as Principal Component Analysis, Independent Component Analysis, Eigenvector Decomposition, or similar may be used to transform a received multi-tracer image into a component space. After this transformation, the components with the most power (largest coefficients) represent the underlying the signal of the image, and components with low power (smaller coefficients) are often dominated by statistical noise. Since the radioactive decay of the individual tracers is present throughout the entirety of the image, this underlying signal of the multi-tracer image will be represented within the components with high power. As such, these components with higher power have been pre-conditioned to represent the decay differences of the tracers and are more amenable to signal separation. Those skilled in the art of regularization will also realize that the components with low power may be suppressed, effectively regularizing the data by suppressing those components that are dominated by noise. As such, these exemplary embodiments may include sub-processes of both regularization and preconditioning.

FIG. 3B shows a flowchart depicting an exemplary embodiment in which preconditioning is applied by transforming the received dual-tracer PET image into principal components (steps S51 and S53), regularization is applied to the components (step S55), and then signal separation factors are determined for each component (step S57). The signal separation factors are then applied to the dual-tracer image in voxel space (not component space) (step S59) in order to achieve the tracer separation (steps S61 and step S63). Those skilled in the art of preconditioning will realize that many other approaches are possible and can be used to practice the preferred embodiments. These include a variety of preconditioning linear and iterative methods, random preconditioning, spectrally equivalent preconditioning, Cholesky factorizations, LU factorizing, over-relaxation and multi-grid techniques, and numerous others.

Feature Preservation (S03-3)

Feature Preservation techniques draw from aspects of feature extraction, component analysis, Tucker- and wavelet-decomposition, and related approaches to identify and preserve sets of image features while processing. In exemplary embodiments of the current invention, feature preservation techniques may be applied in order to ensure that the underlying features present in the received multi-tracer PET data persevere through the signal separation process and remain present in the collection of output individual tracer data. Feature preservation techniques may also be used in order to ensure that image features (such as image artifacts) that are not present in the received multi-tracer digital data do not inadvertently appear in the output individual-tracer data.

In exemplary embodiments, component analysis techniques, similar to those described earlier for component-based preconditioning, may be used to decompose a received multi-tracer image into a set of image components, each with its own weighting coefficient. Each component may be considered an image feature. Feature preservation may be applied during signal separation by adding the constraint that, for each component, the sum of coefficients over all recovered tracers equals the coefficient for the original dual-tracer image. This ensures that the each feature present in the original multi-tracer image is preserved (collectively) over the recovered individual-tracer images, and also that features that are not present in the original dual-tracer image cannot appear in the recovered individual-tracer images.

In other exemplary embodiments, the original multi-tracer image may be decomposed into a set of features using other techniques, such as the use of level sets, edge- and surface-preserving techniques, diffusion-based techniques, and so on. Feature preservation may be used by applying the constraint that the output images for each tracer cannot contain features that were not present in the input image, but the magnitude (i.e. contrast) of the feature is allowed to vary. Those skilled in the art of feature preservation will realize that many other approaches are possible and can be used to practice the preferred embodiments.

FIG. 3C shows a flowchart depicting an exemplary embodiment in which feature preservation is applied with regularization, and signal-separation factors are computed for each feature. The received dual-tracer PET image is decomposed into features (steps S71 and S73) and then the features are regularized (step S75). Signal separation factors are determined for each feature (step S77), and the factors are applied to each feature to achieve separation (step S79). The separated features are then converted back to image voxels (step S81) before generating the output images of each tracer (steps S83 and S85).

Late Tracer Kinetics (S03-4)

In exemplary embodiments, the signal separation step may need to account for any ongoing changes in tracer distributions as well as for radioactive decay of each tracer. For example, it is well known that FDG uptake in some tumors can slowly increase in the second hour after administration, whereas FDG uptake due to inflammatory processes may slowly washout over this same time period. These changes may be referred to as "late kinetic changes", "late tracer kinetics", or "residual kinetics". Unless accounted for, such late tracer kinetics can adversely affect decay-based signal separation and produce unacceptable results.

In exemplary embodiments, Eq 2. may be modified to account for late tracer kinetics. For example, late kinetic changes may be incorporated into $\lambda_1$ and $\lambda_2$, essentially converting the exponential terms from representing radioactive decay to kinetic factors representing decay-plus-residual kinetics. Alternatively, a residual exponential term with $\lambda_{residual}$ may be added to the to the model (so that eqs. 1 and 2 sum over three exponentials, with the third accounting for residual tracer kinetics). In either case, the resulting $\lambda$ parameters are no longer known a priori, but rather become unknown parameters of the model of Eq. 2 and must be estimated as the equation is solved. The recovered parameters are then compared to the known radioactive decay constants of each tracer coupled with tracer-dependent characteristics of possible late kinetic changes, and such late tracer kinetics may thus be assigned to each constituent tracer accordingly.

Several variations of these approaches may be use depending the characteristics of the particular tracers being images. For example, consider a dual-tracer case where tracer 1 is known to be fully fixed (no late kinetic changes), and tracer 2 may be slowly washing out of the tissue. In that case, $\lambda_1$ is known a priori to equal tracer 1's radioactive decay constant, and $\lambda_2$ is known to be greater than or equal to tracer 2's radioactive decay constant. When solving Eq. 2, $\lambda_1$ is fixed and $\lambda_2$ is estimated subject to the constraint that it is greater than or equal to tracer 2's known decay constant. After solving Eq. 2, the resulting activities $A_k$ for each tracer k are then recovered.

As another example, consider the variation where tracer 1 experiences late tracer kinetics where it is slowing washing-in to the tissue, whereas tracer 2 is slowly washing out. In that case, both $\lambda_1$ and $\lambda_2$ are treated as unknowns and estimated when solving Eq. 2, with A subject to the constraint that it is less than or equal to tracer 1's radioactive decay constant, and $\lambda_2$ is subject to the constraint that it is greater than or equal to tracer 2's radioactive decay constant.

In other exemplary embodiments, preconditioning or feature preservation approaches may be modified to account for late tracer kinetics. For example, when preconditioning is applied using a component-analysis technique such as Principal Component Analysis, differences in tracer uptake over time present across the entirety of the image, and as such may be represented by components with high power. When late tracer kinetics are present, these high power components may represent both the radioactive decay and late kinetics of the constituent tracers. As such, each tracer may be represented, at least in part, by different components. By applying additional transformations, such as the technique of Factor Analysis of Dynamic Structures, the components may be rotated to maximize the degree to which individual components represent individual tracers. Signal separation may then be performed by assigning each component to its corresponding tracer. Since both radioactive decay and late tracer kinetics are fundamentally represented by the components themselves, this approach automatically accounts for any late tracer kinetics.

Those skilled in the art of tracer kinetic modeling will realize that many other approaches to accounting for late tracer kinetics are possible and can be used to practice the preferred embodiment In exemplary embodiments, step S03 may result in determination of at least one set of separated digital data, and in some exemplary embodiments may result in determination of at least two sets of separated digital data, where each of the at least two sets of separated digital data corresponds to a different tracer.

Output Data Determination (S04)

In step S04, the system generates at least one set of output digital data based on the determined at least one set of separated digital data, where the at least one set of output digital data represents PET tracer output data for a respective one of the at least two PET tracers associated with the received digital data. In exemplary embodiments, step S04 may result in generation of at least two sets of output digital data, each of the at least two sets of output digital data representing PET tracer output data for a respective one of the at least two PET tracers associated with the received digital data.

Each set of output digital data may represent a single location or measurement item (such as a single voxel or average value over a region), a plurality of voxels over a region, a plurality of voxels representing a two dimensional (2D) image (an image "slice"), or a plurality of voxels representing a three dimensional (3D) image volume (a "volumetric image"). For each of these cases, the set of output digital data may represent a single point in time (such as a static image), or multiple points in time (such as a multi-frame image, a dynamic image, or a time-activity curve).

Each set of output digital data may also be corrected for the effects of radioactive decay.

Example 1

Figure 4A:
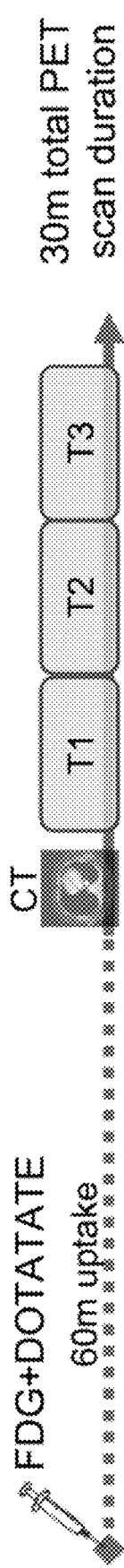
FIGS. 4A and 4B show a simultaneous dual-tracer FDG+ Ga68-DOTATATE scanning approach according to an exemplary embodiment of the present invention.
Figure 4B:
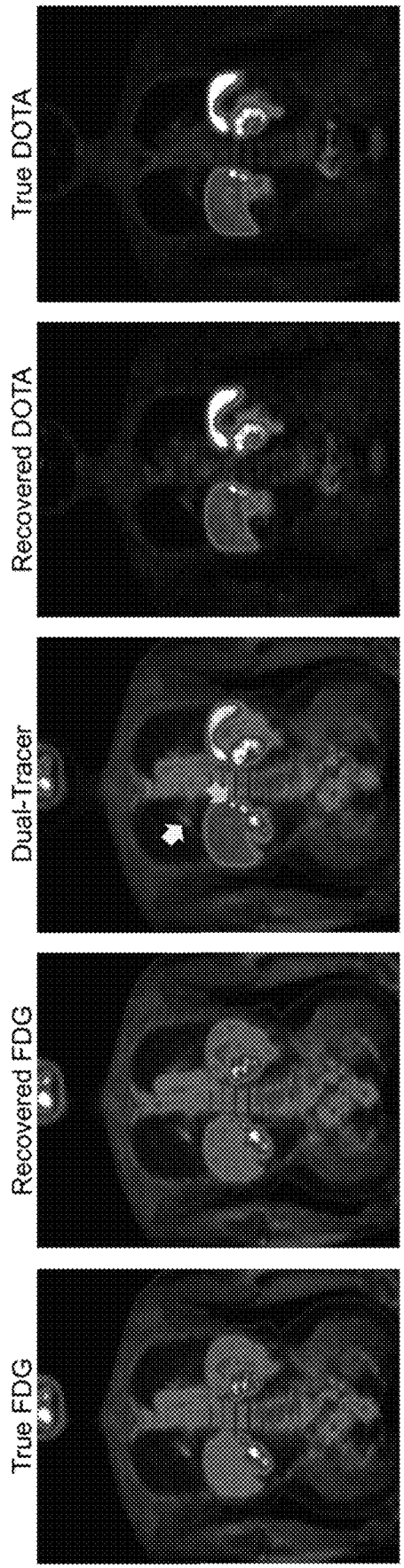

FIGS. 4A and 4B show an example simultaneous dual-tracer FDG+Ga68-DOTATATE scanning approach, including output images of each tracer alongside true images for comparison. FIG. 4A shows the simultaneous scan protocol, and FIG. 4B shows example FDG and DOTATE images for a 30 min simultaneous scan. Each tracer was administered separately in the uptake room. After ~60 min uptake, the patient was positioned on the imaging table with CT scout or topogram, and a CTAC scan (CT for PET attenuation correction) was acquired per usual practice. Multi-timepoint "whole-body" PET scanning then commenced, acquiring three repeat "whole-body" passes over the desired body region. The multi-timepoint whole-body PET data were then reconstructed and sent to mfiVerse™ to recover separate individual-tracer images. The mfiVerse™ software applied dual-tracer signal separation algorithms that recover separate (corrected) images of FDG and either DOTATATE or PSMA from the dual-tracer inputs. These algorithms utilized differences in radioactive decay, coupled with preconditioning and component/feature-preservation techniques, to compute the relative contribution of each tracer to each timepoint for each image voxel. The recovered FDG and DOTATATE images closely matched the true images, with areas of focal uptake (arrows) effectively (but not perfectly) recovered for each tracer. Thus, it was found that FDG and DOTATATE images could be accurately and robustly recovered from simultaneous multi-timepoint imaging.

Example 2

Figure 5:
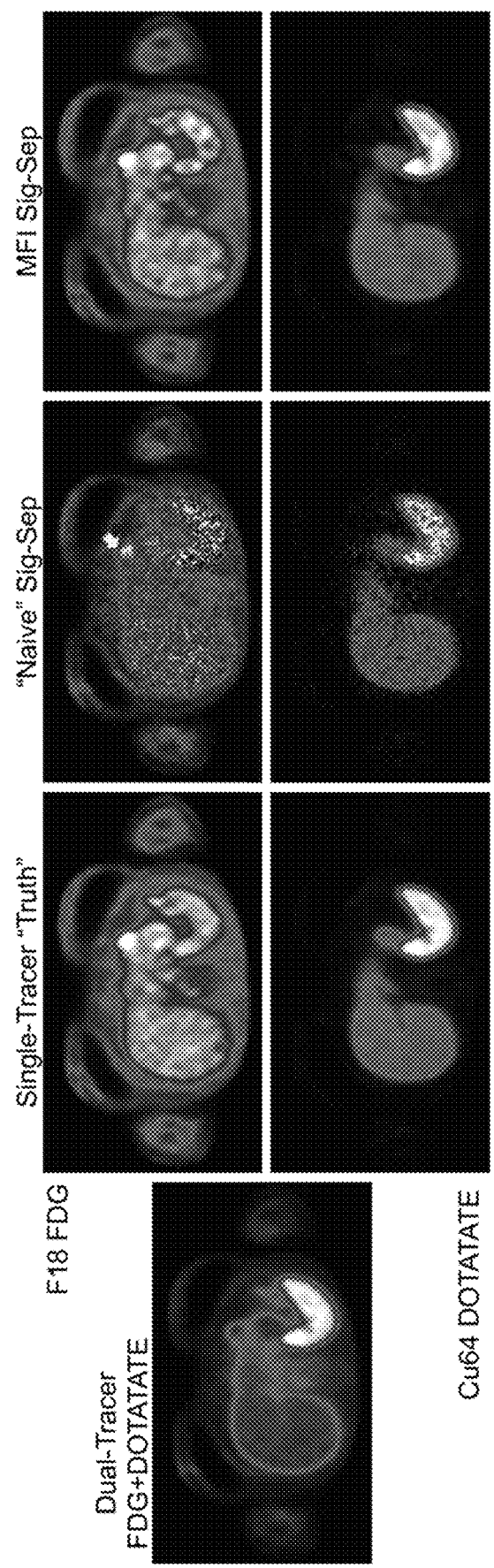
FIG. 5 shows results for simultaneous FDG+DOTATATE for a 3-pass 30-min. duration scan according to an exemplary embodiment of the present invention.

FIG. 5 shows example results for simultaneous FDG+DOTATATE for a 3-pass 30-min. duration scan. Images of each tracer were recovered using both "naïve" decay-based signal separation of Huang et al (1982) and methods of the present invention using preconditioners and regularization with the signal-separation to improve recovery. Quantitative results of voxelwise linear regression analysis and root mean square error (RMSE) for this case are shown in Table 1. These results show the high noise sensitivity of simple decay-based signal separation, which is largely mitigated by the pre-conditioning step. The recovered images and single-tracer "true" images are visually very similar but exhibit some differences in noise patterns and texture.

TABLE 1

Linear Regression Results and RMSE (3 passes × 10m)

| | | Correlation | Slope | Intercept | RMSE |
|---|---|---|---|---|---|
| FDG: | Naïve | 0.819 | 1.002 | 0.0577 | 2.701 |
| | MFI | 0.998 | 1.007 | −0.0017 | 0.553 |
| DOTATATE: | Naïve | 0.819 | 0.678 | 0.0564 | 2.496 |
| | MFI | 0.990 | 0.983 | 0.0015 | 0.529 |

(Intercept, RMSE units = kBq/cc)

Now that embodiments of the present invention have been shown and described in detail, various modifications and improvements thereon will become readily apparent to those skilled in the art. Accordingly, the spirit and scope of the present invention is to be construed broadly and not limited by the foregoing specification.

The invention claimed is:

1. A method comprising:
A) receiving, at one or more computers, digital data generated by positron emission tomography (PET) scans of a region of interest of a physiologic body which has been administered at least two PET tracers that differ from one another at least in their radioactive decay constant, the digital data comprising PET information associated with at least two time points, the at least two time points obtained after the administration of the at least two PET tracers and subsequent to initial wash-in phase of distribution throughout the body;
B) determining, by the one or more computers, based on the radioactive decay constants of each PET tracer, at least two sets of output digital data, each of the at least two sets of output digital data corresponding to each of the at least two PET tracers, the step of determining comprising at least one of the following sub-steps:
  i. regularizing to account for statistical noise;
  ii. preconditioning the digital data to be more amenable to signal separation;
  iii. applying feature preservation techniques; or
  iv. accounting for late tracer kinetics; and
C) generating, by the one or more computers, at least two images, each of the at least two images corresponding to one of the at least two sets of output digital data, each of the two images indicating a PET tracer data within the region of interest for a respective one of the at least two PET tracers associated with the at least two time points, wherein the at least two images are static images, or wherein the at least two images are dynamic images, or wherein the at least two images comprise at least one static image and at least one dynamic image.

2. The method of claim 1, wherein the at least two images are static images.

3. The method of claim 1, wherein the at least two images are dynamic images.

4. The method of claim 1, wherein the at least two images comprise a static image and a dynamic image.

5. The method of claim 1, wherein the at least two images are decay corrected.

6. The method of claim 1, wherein a kinetic factor for at least one of the at least two PET tracers is allowed to differ from the known radioactive decay constant in order to account for late tracer kinetics.

7. The method of claim 6, wherein the kinetic factor for at least one of the at least two PET tracers is constrained to be equal to or larger than that tracer's known radioactive decay constant.

8. The method of claim 6, wherein the kinetic factor for at least one of the at least two PET tracers is constrained to be equal to or smaller than that tracer's known radioactive decay constant.

9. The method of claim 6, wherein the kinetic factor for at least one of the at least two PET tracers is constrained to be equal to or larger than that tracer's known radioactive decay constant, and the kinetic factor for at least one other PET tracer is constrained to be less than or equal to that tracer's known radioactive decay constant.

10. The method of claim 1, further comprising, at a time subsequent to step A), a step of co-registering the image data over the at least two time points to correct for patient motion.

11. The method of claim 1, wherein in B) determining is performed independently for each set of received digital data.

12. The method of claim 1, wherein the region of interest comprises a voxel.

13. The method of claim 1, wherein the digital data comprises tracer activity, tracer activity concentration, or tracer uptake.

14. The method of claim 1, wherein one tracer of the at least two PET tracers is F18-Fluorodeoxyglucose.

15. The method of claim 14, wherein another tracer of the at least two PET tracers images prostate-specific membrane antigen (PSMA) expression.

16. The method of claim 15, wherein the tracer that images prostate-specific membrane antigen (PSMA) expression comprises a tracer selected from the listing consisting of: Ga68-labeled PSMA ligands, Ga68-PSMA-11, Ga68-PSMA-617, Ga68-PSMA-I&T, F18-piflufloflastat, F18-flotufolastat, F18-PSMA-1007, and F18-fluciclovine.

17. The method of claim 1, wherein at least one tracer of the at least two PET tracers images prostate-specific membrane antigen (PSMA) expression.

18. A system comprising:
one or more processors; and
a non-transitory computer readable memory operatively connected to the one or more processors and containing instructions stored thereon for the one or more processors to carry out a process comprising:
  A) receiving, at one or more computers, digital data generated by positron emission tomography (PET) scans of a region of interest of a physiologic body which has been administered at least two PET tracers that differ from one another at least in their radioactive decay constant, the digital data comprising PET information associated with at least two time points, the at least two time points obtained after the administration of the at least two PET tracers and subsequent to initial wash-in phase of distribution throughout the body;
  B) determining, by the one or more computers, based on the radioactive decay constants of each PET tracer, at least two sets of output digital data, each of the at least two sets of output digital data corresponding to each of the at least two PET tracers, the step of determining comprising at least one of the following sub-steps:
    i. regularizing to account for statistical noise; or
    ii. preconditioning the digital data to be more amenable to signal separation;
    iii. applying feature preservation techniques;
    iv. accounting for late tracer kinetics; and
  C) generating, by the one or more computers, at least two images, each of the at least two images corresponding to one of the at least two sets of output digital data, each of the two images indicating a PET tracer data within the region of interest for a respective one of the at least two PET tracers associated with the at least two time points, wherein the at least two images are static images, or wherein the at least two images are dynamic images, or wherein the at least two images comprise at least one static image and at least one dynamic image.

* * * * *

UNITED STATES PATENT AND TRADEMARK OFFICE
CERTIFICATE OF CORRECTION

| | | |
|---|---|---|
| PATENT NO. | : 12,086,990 B1 | Page 1 of 1 |
| APPLICATION NO. | : 18/643544 | |
| DATED | : September 10, 2024 | |
| INVENTOR(S) | : Dan J. Kadrmas | |

It is certified that error appears in the above-identified patent and that said Letters Patent is hereby corrected as shown below:

In the Specification

Column 1, Line 5, insert:
--GOVERNMENT SUPPORT STATEMENT
This invention was made with government support under R44 CA257522 and R43 CA257522 awarded by the National Institutes of Health. The government has certain rights in the invention.--

Signed and Sealed this
Thirty-first Day of December, 2024

Derrick Brent
*Acting Director of the United States Patent and Trademark Office*